United States Patent [19]

Asami et al.

[11] Patent Number: 4,774,185
[45] Date of Patent: Sep. 27, 1988

[54] NOVEL SUPEROXIDE DISMUTASE AND PROCESS FOR PREPARATION THEREOF

[75] Inventors: Sumio Asami, Ibaraki; Norihide Amano, Takatsuki; Teruo Amachi, Takarazuka; Hajime Yoshizumi, Takatsuki, all of Japan

[73] Assignee: Suntory Limited, Osaka, Japan

[21] Appl. No.: 915,026

[22] Filed: Oct. 3, 1986

[30] Foreign Application Priority Data

Oct. 4, 1985 [JP] Japan ............... 60-220215

[51] Int. Cl.$^4$ ............... C12N 9/02; C12R 1/01
[52] U.S. Cl. ............... 435/189; 435/822
[58] Field of Search ............... 435/189, 822

[56] References Cited

U.S. PATENT DOCUMENTS 4,563,349 1/1986 Miyata et al. ............... 435/189 X

FOREIGN PATENT DOCUMENTS 55-35983 5/1980 Japan.
57-29285 1/1982 Japan.

OTHER PUBLICATIONS

ATCC Catalogue of Bacteria, 16th edition, 1985, pp. 123–124.
Chemical Abstracts, vol. 98, No. 5, Jan. 1983, "Purification and Properties of a Unique Superoxide Dismutase from Nocardia Asteroides".
E. M. Gregory et al, J. Bacteriol., vol. 117, No. 2, pp. 456–460.

Primary Examiner—Thomas G. Wiseman
Assistant Examiner—Charles Patterson
Attorney, Agent, or Firm—Burns, Doane, Swecker & Mathis

[57] ABSTRACT

A novel superoxide dismutase prepared from a superoxide dismutase-producing strain of the genus Nocardiopsis. The enzyme is a tetramer with a molecular weight of about $8.8 \times 10^4$, composed of sub-units of about $2.2 \times 10^4$. The superoxide dismutase contains 1.56 g-atoms of iron per mole but no copper or manganese. Potassium cyanide at a concentration of 1 mM does not inhibit activity, however exponential inactivation is caused by 5 mM hydrogen peroxide.

5 Claims, 3 Drawing Sheets

TEMPERATURE STABILITY

ABSORBANCE SPECTRUM

INACTIVATION WITH HYDROGEN PEROXIDE

NOVEL SUPEROXIDE DISMUTASE AND PROCESS FOR PREPARATION THEREOF

BACKGROUND OF THE INVENTION

1. Field of the Invention

The present invention relates to a novel superoxide dismutase (hereinafter referred to as "SOD") and a process for the preparation thereof.

2. Description of the Related Art

SOD is an enzyme disproportionating two superoxide radicals into a hydrogen peroxide and a molecular oxygen, and it is known that SOD is widely present in animals, plants and microorganisms. The superoxide radical is an important agent of toxicity of oxygen generated in an organism, and it is understood that SOD protects an organism from the superoxide radical have been recently elucidated, and the role of SOD as the organism defending enzyme has attracted attention. For example, it has been found that SOD effectively protects against oxidation easily oxidizable substances such as foodstuffs (Japanese Unexamined Patent Publication No. 5-40785), as a cosmetic component for protecting the skin and hair, controlling pigmentation on the skin, exerting an anti-inflammatory action to the skin and preventing putrefaction of components of a cosmetic composition (Japanese Unexamined Patent Publications No. 51-63949 and No. 55-87712) and for the remedy of rheumatoid arthritis (M. Walravents & J. Dequeker, Current Therapeutic Res., 20 62–69, 1976).

SOD is a metal-containing enzyme and is divided into three types, copper (Cu)-zinc (Zn)-SOD, manganese (Mn)-SOD, and iron (Fe)-SOD, according to the kind of metal contained therein. It is known that Cu, Zn-SOD is present in the cytoplasm of eucaryotes, Mn-SOD is present in the mitochondria of eucaryotes, algae and prokaryotic cells, and Fe-SOD is present in algaes and prokaryotic cells. However, the SOD of the present invention has not been known.

SUMMARY OF THE INVENTION

The present invention provides, therefore, a novel superoxide dismutase having the following properties:

(a) action: the superoxide dismutase disproportionates two superoxide radicals to a hydrogen peroxide and a molecular oxygen;

(b) substrate specificity: the superoxide dismutase acts on a superoxide radical;

(c) optimum pH: the optimum pH is about 8;

(d) stable pH: the superoxide dismutase is stable at pH of 4.5 to 8.0 (when the superoxide dismutase is treated at 25° C. for 60 minutes, the residual activity is at least 80%);

(e) thermal stability: when the residual activity is measured after the heat treatment for 10 minutes at pH 7.8, the superoxide dismutase is stable at treatment temperatures of up to about 50° C. and the residual activity is 90% at a treatment temperature of 60° C. and 50% at a treatment temperature of 70° C.;

(f) molecular weight: the molecular weight is about $8.8 \times 10^4$, as determined according to the gel filtration method;

(g) absorption spectrum at ultraviolet and visible regions: the maximum absorbance appears at about 280 nm, the minimum absorbance appears at about 250 nm, and a shoulder appears at about 290 nm;

(h) molecular extinction coefficient: the molecular extinction coefficient at 280 nm is about $1.45 \times 10^5$ $M^{-1}cm^{-1}$;

(i) inhibition: the activity is not inhibited by the addition of 1 mM potassium cyanide and exponential deactivation is caused with the lapse of time by the addition of 5 mM hydrogen peroxide; and (j) metal analysis: the superoxide dismutase contains 1.56 g-atoms of iron per mole of the enzyme but does not contain copper and manganese.

The present invention also provides a process for the preparation of the above-mentioned superoxide dismutase, which comprises culturing a superoxide dismutase-producing strain belonging to the genus Nocardiopsis in a culture medium to form and accumulate the superoxide dismutase in the culture medium, and recovering the superoxide dismutase from the culture medium,

DESCRIPTION OF THE PREFERRED EMBODIMENT

The foregoing object is attained by a novel SOD having the properties described in detail hereinafter, and a process for production thereof by using strains belonging to the genus Nocardiopsis.

With a view to obtaining a valuable SOD producing organism, the present inventors searched for microorganisms having a high SOD-producing property broadly in the natural source, and as a result, the present inventors found that strains belonging to the genus Nocardiopsis, which was isolated from the soil of Yakushima, Kagoshima Prefecture, Japan, produces a novel SOD in a large quantity.

The properties of the SOD obtained according to the present invention will now be described.

(a) Action

The enzyme disproportionates two superoxide radicals into a hydrogen peroxide and a molecualr oxygen.

(b) Substrate Specificity

The enzyme acts on a superoxide radical.

(c) Optimum pH

The optimum pH of the enzyme is about 8.

(d) Stable pH Range

Figure 1:
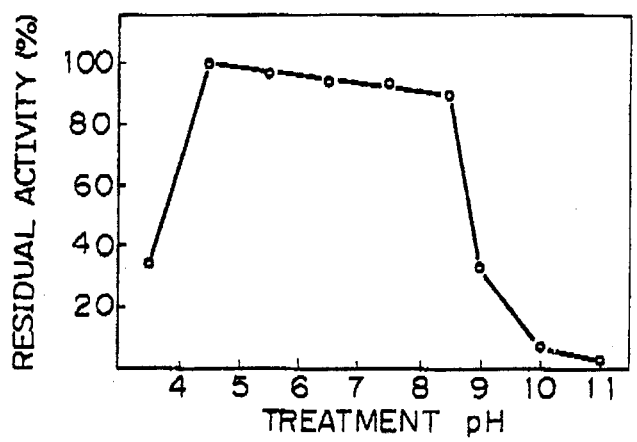
FIG. 1 is a graph showing the pH stability of the SOD of the present invention.

At a pH of 4.5 to 8.0, the residual activity is higher than 80% when the enzyme is treated at 25° C. for 60 minutes (see FIG. 1).

(e) Thermal Stability

Figure 2:
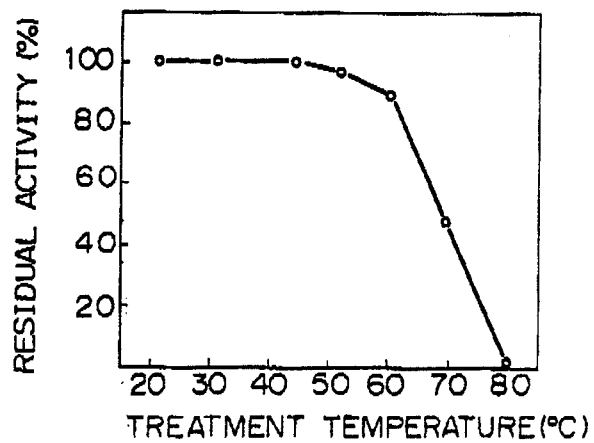
FIG. 2 is a graph showing the thermal stability of the SOD of the present invention.

When the enzyme is heat-treated at a pH of 7.8 for 10 minutes, the enzyme is stable at temperatures of up to about 50° C., and the residual activity is 90% at 60° C. and 50% at 70° C. (see FIG. 2).

(f) Molecular Weight

The molecular weight is about 88,000 as determined by the gel filtration method by high performance liquid chromatography using Shimpak DIOL 150 (supplied by Shimazu Seisakusho) equilibrated with a 0.01M phosphate buffer containing 0.2M sodium chloride at a pH of 7.0. Furthermore, a molecular weight of about 22,000 is obtained by treating the enzyme with 1% sodium lauryl sulfate (hereinafter referred to as SDS) and carrying out the polyacrylamide gel electrophoresis in the presence of SDS (*The Journal of Biological Chemistry*, 244, 5074–5080, 1969). From these results, it is confirmed that the enzyme of the present invention is a tetramer of sub-units having a molecular weight of about 22,000.

(g) Absorption Spectrum in Ultraviolet and Visible Region

Figure 3:
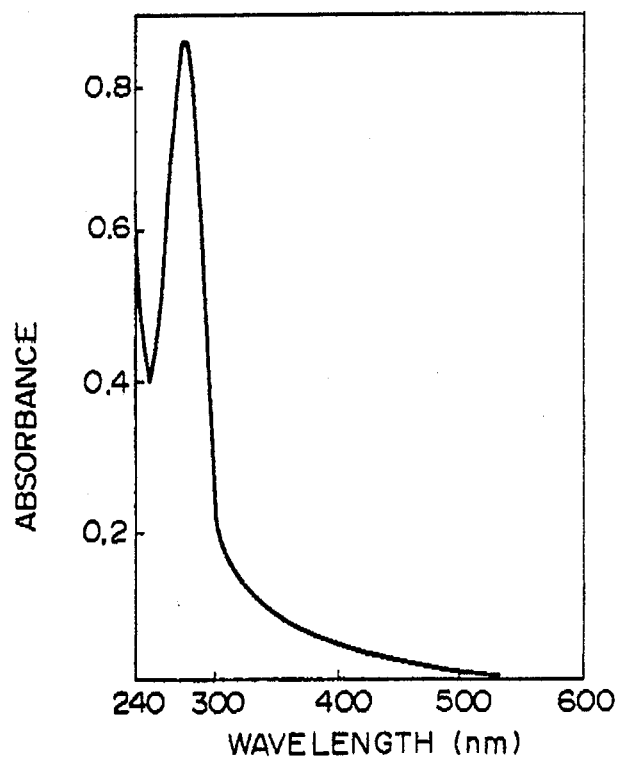
FIG. 3 shows the absorption spectrum in ultraviolet and visible region of the SOD of the present invention.

As shown in FIG. 3, a maximum absorbance appears in the vicinity of 280 nm, a minimum absorbance appears in the vicinity of 250 nm, and a shoulder appears in the vicinity of 290 nm.

(h) Molecular Extinction Coefficient

The molecular extinction coefficient of the enzyme at 280 nm is about $1.45 \times 10^5 \, M^{-1} cm^{-1}$.

(i) Inhibition of Activity by Potassium Cyanide

According to the cytochrome C method described hereinafter, the activity is not inhibited by adding 1 mM potassium cyanide to the reaction mixture.

(j) Inactivation by Hydrogen Peroxide

Figure 4:
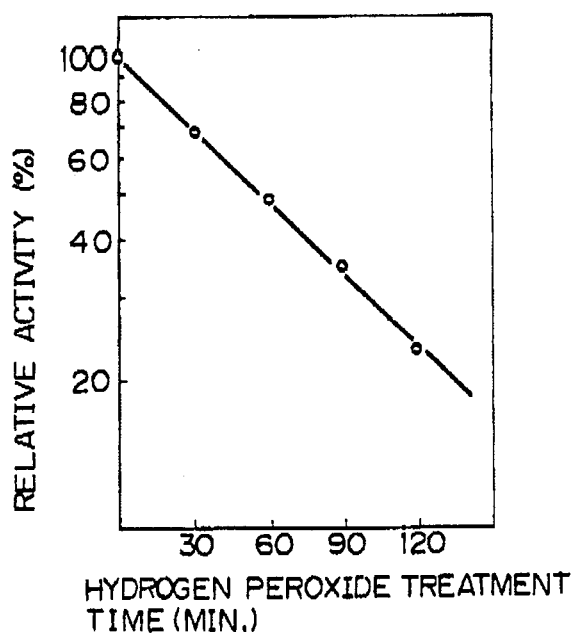
FIG. 4 shows the inactivation profile of the SOD of the present invention by the hydrogen peroxide treatment.

When hydrogen peroxide is added to a solution of the enzyme so that the hydrogen peroxide concentration is 5 mM and the activity is measured by the cytochrome C method described hereinafter, the enzyme is exponentially inactivated with the lapse of time (FIG. 4).

(k) Metal Analysis

According to the atomic extinction analysis method, it is confirmed that the enzyme contains 1.56 g-atoms of iron per mole of enzyme and does not contain copper and manganese.

The methods for measuring the activity of the SOD of the present invention will now be described.

(1) Cytochrome C Method

The measurement is carried out according to the method disclosed in *The Journal of Biological Chemistry*, 244, 6049–6055, 1969. More specifically, a reaction mixture (0.4 ml) is prepared so that the final concentrations are 50 mM phosphate buffer (pH 7.8), 0.1 mM sodium ethylenediamine tetraacetate, 10 μm ferricytochrome C and 50 μm xanthine, and an enzyme solution (50 μl) diluted within the measurable range with phosphate buffer is added so that the total volume is 0.5 ml. At 25° C., the initial rate (v) of increase of the absorbance at 550 nm due to a reduction of cytochrome C is measured by a spectrophotometer. Furthermore, the initial rate (V) of increase of the above absorbance observed when a phosphate buffer (pH 7.8) is added instead of the enzyme solution is measured. The amount of the enzyme inhibiting by 50% the initial rate of increase of the absorbance due to reduction of cytochrome C under the above-mentioned reaction conditions is defined as 1 unit (u), and the activity of the enzyme can be determined from the formula $(V/v - 1)$. Note, in this cytochrome C method, when a crude product such as a supernatant of a culture medium is used, vigorous interference is caused by impurities and the activity cannot be correctly measured. Accordingly, during the purification process, especially during the initial purification process, the activity is measured according to the following method.

(2) Nitro Blue Tetrazolium (NBT) Method

The measurement is carried out according to a modification of the method disclosed in *Biochemical and Biophysical Research Communications*, 46, 839–854, 1972. Namely, a reaction mixture (0.4 ml) is prepared so that the final concentrations are 0.1M phosphate buffer (pH 7.5), 6 μm phenazine mesosulfate and 0.1 mM nitro blue tetrazolium, an enzyme solution (50 μl) diluted within the measurable range with a phosphate buffer (pH 7.0) is added, and a solution (50 μl) of 1.6 mM nicotinamide adeninedinucleotide (reduced form) is further added so that the total volume is 0.5 ml. The initial rate of increase of the absorbance at 560 nm due to the reduction of nitro blue tetrazolium was measured by a spectrophotometer. As a control, the initial rate of increase of the above absorbance observed when a phosphate buffer (pH 7.0) is added instead of the enzyme liquid is measured. The activity of the enzyme is calculated in the same manner as described above with respect to the cytochrome C method.

The protein is determined according to the Lowry method (*The Journal of Biological Chemistry*, 193, 265–275, 1951).

The taxonomical properties of the SAM-0081 strain as a typical representative of the strains producing the above-mentioned novel SOD will now be described.

1. Morphology

Aerial hyphae has a diameter of 0.4 to 0.7 μm. The form of the aerial hyphae is simple and not verticillate. Spore chains are found on the top end of aerial mycelium. Form of spore chains is spiral. Each chain ordinarily contains at least 10 spores. Fragmentation of substrate mycelium is not observed. Sporangia or flagellated spores are not observed. Under an electron microscope, the spore surface is seen warty. The spore has a cylindrical to short cylindrical shape and has a length of 0.9 to 1.7 μm and a width of 0.6 to 1.1 μm.

2. Growth on Various Media

The properties on various culture media are shown in Table 1. Incidentally, the observation was carried out after culturing had been conducted at 30° C. for 7 days.

TABLE 1

| Culture Medium | Aerial Mycelium Formation | Aerial Mycelium Color | Reverse Color | Soluble Pigment | Others |
| --- | --- | --- | --- | --- | --- |
| Sucrose-nitrate agar medium | scant | white | yellow | none | |
| Glucose-asparagine agar medium | absent | — | white to yellow | none | |
| Glycerol-asaparagine agar medium | thin | white | brownish yellow | orange yellow | |
| Inorganic salts-starch agar medium | thin | white to gray | yellow | none | wrinkled on both surface and reverse of the colony |
| Tyrosine agar medium | scant | white | grayish yellow | none | |
| Nutrient agar medium | thin | white | light yellow | none | |
| Yeast extract-malt extract agar medium | abundant | dark gray to grayish white | grayish yellow | none | |
| Oatmeal agar medium | thin | gray | orange yellow | none | |

3. Physiological Properties (1) Growth temperature range (7 days' culturing in CYC liquid medium)
growth-possible temperature: 16°–51° C.
optimum growth temperature: 24°–37° C.
(2) Liquefaction of gelatin
positive
(3) Hydrolysis of starch
positive
(4) Coagulation of skim milk
negative
(5) Peptonization of skim milk
positive
(6) Formation of Melanoid pigments
positive in Peptone-yeast extract iron agar medium, and positive in Tyrosine agar medium
(7) Reduction of nitrate
negative 4. Utilization of Carbon Sources (7 days' culturing at 28° C. in Pridham-Gottlieb agar medium)
L-arabinose: ++
D-xylose: +
D-glucose: ++
D-fractose: ++
sucrose: ++
inositol: ++
L-rhamnose: ++
raffinose: ++
D-mannitol: ++
D-galactose: ++
salicin: −

Note
++: strongly positive utilization,
+: positive utilization,
−: utilization negative 5. Cell Wall Analysis According to the method of J.L. Staneck and G.D. Roberts, *Applied Microbiology*, 28, 226–231, 1974, an isomer of 2,6-diaminopymellic acid is examined, and it is found that the isomer is of the mesotype. According to the above-mentioned method, the whole cells are hydrolyzed and analyzed by thin layer chromatography. Ribose and glucose are apparently detected and a trace of galactose is detected.

From the above-mentioned analysis, it is seen that strain SAM-0081 has Type III cell wall and wholecell sugar protein C.

6. Quinone System

When the quinone system is analyzed according to the method of Yuzo Yamade and Susumu Kuraishi (*Experiments for Chemotaxomomy of Microorganisms*, 143–155, 1982, edited by Kazuo Komagata and published by Gakkai Shuppan Center), it is found that the strain SAM 0081 contains menaquinone MK-9 ($H_8$) as the major component and MK-9 ($H_6$, $H_4$, $H_{10}$) as the minor component.

When the taxonomic position of SAM-0081 is determined based on the above-mentioned taxonomical properties, referring H.A. Lechevalier and M.P. Lechevalier, Introduction to the Order Actinomycetales, "The Prokaryots A Handbook of Habitats, Isolation, and Identification of Bacteria", 1915–1922, 1981, edited by M. P. Starr et al and published by Springer-Verlag, Berlin, it is found that the present strain is very similar to actinomycetes belonging to the genus Nocardiopsis in that the cell wall is of type III, madurose is not detected in the whole cell hydrolysate and long spore chains are formed on the top ends of aerial mycelia. However, although microorganisms belonging to the genus Nocardiopsis are defined to have menaquinone MK-10 ($H_4$) or MK-10 ($H_6$) as the major component of the quinone system, the major component of the quinone system of the present strain is menaquinone MK-9 ($H_8$). Moreover, a species having spiral spore chain on the top ends of aerial mycelia, which belongs to the genus Nocardiopsis, is not known, and it may not be denied that the present strain will be assigned to a new genus. However, at the present, it is deemed most reasonable to identify the present strain as a species belonging to the genus Nocardiopsis. Accordingly, the present inventors identified the strain SAM-0081 as a species of the genus Nocardiopsis, which is mainly characterized in that spiral spore chains of at least 10 spores are formed on the top end of aerial mycelium, fragmentation of substrate mycelia is ordinarily not observed, and the major component of the quinone system is menaquinone MK-9 ($H_8$) and the minor component is MK-9 ($H_6$, $H_4$, $H_{10}$). This strain is designated "SAM-0081".

The strain SAM-0081 was deposited at Fermentation Research Institute (FRI), Agency of Industrial Science and Technology, Ministry of International Trade and Industry (1-3, Higashi 1-chome, Yatabe-machi, Tsukubagun, Ibaraki-ken, 305, JAPAN) with deposition number FERM P-8426 on Aug. 24, 1985, and transferred to the international deposition under Budapest Treaty on Aug. 12, 1986, as FERM BP-1151.

The process for preparing SOD by using the above-mentioned strains (hereinafter referred to as "present strains") will now be described.

The preparation of SOD is accomplished by culturing the present strain in a culture medium, recovering the intended product produced in the medium, and purifying it.

A liquid or solid culture medium containing nutrient sources can be used for culturing the present strain. However, when culturing is conducted on a large scale, a liquid medium is preferred.

Nutrients that can be utilized by the present strain, that is, carbon sources, nitrogen sources, inorganic salts and trace nutrient elements, are incorporated into the culture medium. Starch, glucose and sucrose can be used as the carbon source, and nitrogen-containing substances such as corn steep liquor, yeast extract, yeast cells, casein, peptones and ammonium sulfate can be used as the nitrogen source. As the inorganic salt, there can be mentioned sodium chloride, potassium phosphate, magnesium sulfate, manganese chloride, iron sulphate, and calcium chloride. As the trace nutrient elements, there can be mentioned vitamins such as vitamin $B_1$ and vitamin $B_2$. Adecanol (registered trademark of the product of Asahi Denka Kogyo Kabushiki Kaisha) may be used as a defoamer.

Culturing is carried out by stationary culturing, shaking culturing, or aeration-agitation culturing, but when culturing is conducted on an industrial scale, submerged aeration-agitation culturing is advantageous. Culturing conditions differ according to the composition of the culture medium and the culturing method. Generally, the culturing temperature is 20° to 40° C., the culturing time is 1 to 5 days, and the pH of the medium is 4 to 9, more preferably 6 to 8.

The SOD of the present invention produced by the present strains is mainly secreted outside the cells. The enzyme is separated and purified by a customary purifying means. More specifically, after culturing, cells and other solid matters contained in the culture medium are removed from the cultured broth by centrifugation or filtration. The resulting supernatant or filtrate is subjected to purification by appropriately combining known separating and purifying means such as salting-out using ammonium sulfate, precipitation using an organic solvent such as acetone, isoelectric precipitation, membrane treatment such as dialysis or electric dialysis, adsorption using calcium phosphate or alumina, ion exchange chromatography using diethylaminoethyl (hereinafter referred to as "DEAE") cellulose, and gel filtration using Sephadex (supplied by Pharmacia) or Ultrogel (supplied by LKB), whereby an enzyme having a purification level meeting the intended object can be obtained.

The present invention provides a novel SOD. Preparation of the SOD by strains belonging to the genus Nocardiopsis has not previously been known. The present invention further provides a novel process for the preparation of SOD. According to this process, SOD is mainly accumulated outside cells. Therefore, the SOD can be recovered and purified very easily.

The present invention will now be described in detail with reference to the following examples.

EXAMPLE 1

10 ml each of a liquid culture medium (adjusted to pH 7.0) containing 3 g/l glucose, 10 g/l corn starch, 2 g/l yeast extract, 10 g/l polypeptone (Takeda Chemical), 3 g/l dry yeast cell and 1 g/l of dipotassium phosphate were distributed into 200 test tubes having a diameter of 25 mm, steam sterilization was carried out at 120° C. for 15 minutes, and the culture medium was inoculated with the present strain. Shaking culturing (300 rpm) was carried out at 28° C. for 91 hours. After termination of the culturing, cells were removed by centrifugation to obtain 1500 ml of a supernatant. The SOD activity of the supernatant was 83 $\mu$/ml as determined according to the NBT method.

Ammonium sulfate was added to the supernatant at a concentration corresponding to 80% of the saturation concentration, and the formed precipitate was collected by centrifugation. The precipitate was dissolved in a small amount of 20 mM phosphate buffer (pH 7.0) and dialyzed in the same buffer. The internal liquid of the dialysis was charged onto a column (2.4 cm $\times$ 15 cm) of DEAE cellulose (DE-23 supplied by Wattman) equilibrated with the same buffer, and the column was washed with 500 ml of the same buffer and eluted with the same buffer at a linear concentration gradient of 0 to 1M sodium chloride, and 136 ml of fractions having an enzyme activity were collected. The fractions were combined, and ammonium sulfate was added to the combined fraction again at a concentration corresponding to 80% of the saturation concentration, and the formed precipitate was collected by centrifugation and dissolved in a small amount of water and dialyzed in water. The internal liquid of the dialysis was lyophilized to obtain 172 mg of a powdery product. The specific activity of the powdery product was 256 $\mu$/mg protein as determined according to the NBT method (3950 $\mu$/mg protein as determined according to the cytochrome C method). The product was dissolved in a phosphate buffer (pH 7.0) containing 0.2M sodium chloride and the solution was charged onto a column (1.1 cm $\times$ 140 cm) of Ultrogel ACA-44 (supplied by LKB) equilibrated with the same buffer, and the column was eluted with the same buffer to obtain 118 ml of fractions having an enzyme activity. The fraction were combined, and the combined fraction was dialyzed and lyophilized to obtain 56 mg of a powdery product. The specific activity of the product was 2700 $\mu$/mg as determined according to the cytochrome C method.

EXAMPLE 2

200 ml each of the same liquid medium as used in Example 1 was distributed into five 500 ml Meyer flasks, and the liquid medium was sterilized and inoculated with the present strain. Culturing was conducted at 28° C. for 71 hours in a rotary shaker at 300 rpm to form an inoculum. Separately, 30 l of the same culture medium was charged in a 50 l fermenter, sterilized, and inoculated with the above-mentioned inoculum. Aerationagitation culturing was conducted at temperature of 30° C. and an aeration rate of 0.5 vvm for 30 hours. After the termination of culturing, cells were removed by centrifugation to obtain 27 l of a supernatant. The SOD activity of the supernatant was 60 $\mu$/ml as determined according to the NBT method. In the same manner as in Example 1, ammonium sulfate was added to the supernatant at a concentration corresponding to 90% of the saturation concentration, and the formed precipitate was recovered by centrifugation. The precipitate was dialyzed in water and the internal liquid of the dialysis was charged onto a column (15 cm $\times$ 170 cm) of a DEAE type polymer resin (FP-DA13 supplied by Mitsubishi Kasei Kogyo) equilibrated with a 20 mM phosphate buffer (pH 7.0), and the column was washed with 7 l of the same buffer and eluted with a 20 mM phosphate buffer (pH 7.0) containing 0.3M sodium chloride to obtain 5 l of fractions having an enzyme activity. The fractions were combined, and the combined fraction was concentrated to 370 ml by ultrafiltration using a PELLICON CASSET SYSTEM (supplied by Millipore; having a pore size of $10^4$, 60 cm$^2 \times 4$), and ammonium sulfate was added at a concentration corresponding to 90% of the saturation concentration. The formed precipitate was collected by centrifugation, and a 10 mM phosphate buffer (pH 7.0) was added to the precipitate to form 100 ml of a solution. 20 ml of the solution was charged onto a column (3.1 cm $\times$ 135 cm) of Ultrogel ACA44 equilibriated with the same buffer containing 0.2M sodium chloride and eluted with the same buffer. The same procedure was repeated to obtain 400 ml as a whole of a fraction having an enzyme activity. The fraction was dialyzed and lyophilized to obtain 1.2 g of SOD preparation. The specific activity of the product was 2400 $\mu$/mg as determined according to the cytochrome C method. The obtained SOD product had the above-mentioned physical properties and enzymological properties and this product was different from known SOD and thus was novel.

We claim:

1. A novel superoxide dismutase having the following properties:
   (a) action: the superoxide dismutase disproportionates two superoxide radicals to a hydrogen peroxide and a molecular oxygen;
   (b) substrate specificity: the superoxide dismutase acts on a superoxide radical;
   (c) optimum pH: the optimum pH is about 8;
   (d) stable pH: the superoxide dismutase is stable at pH of 4.5 to 8.0 (when the superoxide dismutase is treated at 25° C. for 60 minutes, the residual activity is at least 80%);
   (e) thermal stability: when the residual activity is measured after a heat treatment for 10 minutes at a pH of 7.8, the superoxide dismutase is stable at treatment temperature of up to about 50° C., and the residual activity is 90% at a treatment temperature of 60° C., and 50% at a treatment temperature of 70° C.;

(f) molecular weight: the molecular weight is about $8.8 \times 10^4$, as determined according to a gel filtration method;

(g) absorption spectrum of ultraviolet and visible region: the maximum absorbance appears at about 280 nm, the minimum absorbance appears at about 250 nm, and a shoulder appears at about 290 nm;

(h) molecular extinction coefficient: the molecular extinction coefficient at 280 nm is about $1.45 \times 10^5$ $M^{-1}cm^{-1}$;

(i) inhibition: the activity is not inhibited by an addition of 1 mM potassium cyanide and exponential inactivation is caused with the lapse of time by an addition of 5 nM hydrogen peroxide; and (j) metal analysis: the superoxide dismutase contains 1.56 g-atoms of iron per mole of enzyme but does not contain copper and manganese.

2. A process for the preparation of a superoxide dismutase of claim 1, which comprises culturing Nocardiopsis sp. SAM-0081 (FERM BP-1151) in a culture medium to form and accumulate the superoxide dismutase in the culture medium, and recovering the superoxide dismutase from the culture medium.

3. A process according to claim 2, wherein the culturing is carried out in a liquid medium.

4. A process according to claim 2, wherein the recovery is effected by separating the culture medium into a supernatant or filtrate and a precipitate, and the superoxide dismutase is isolated from the supernatant or filtrate.

5. A process according to claim 4, wherein the superoxide dismutase is recovered from the supernatant or filtrate by salting-out, gel filtration and/or ultrafiltration

* * * * *